US005541226A

United States Patent [19]
Williams et al.

[11] Patent Number: 5,541,226
[45] Date of Patent: Jul. 30, 1996

[54] TOPICAL COMPOSITIONS FOR RE-EPITHELIALIZATION OF PERSISTENT EPITHELIAL DEFECTS

[75] Inventors: Patricia B. Williams, Norfolk; Earl R. Crouch, Virginia Beach, both of Va.

[73] Assignee: Center for Innovative Technology, Herndon, Va.

[21] Appl. No.: 312,499

[22] Filed: Sep. 26, 1994

Related U.S. Application Data

[63] Continuation of Ser. No. 55,717, Apr. 30, 1993, abandoned.
[51] Int. Cl.$^6$ .................................................. A61K 31/195
[52] U.S. Cl. ............................................................. 514/561
[58] Field of Search ............................................. 514/561

[56] References Cited

U.S. PATENT DOCUMENTS 4,171,377  10/1979  Green et al. ............................ 424/319

FOREIGN PATENT DOCUMENTS

0275054A1  7/1988  European Pat. Off. .
WO92/09307  6/1992  WIPO .

OTHER PUBLICATIONS

Moses et al; 1985, Ann Ophtamol, vol. 17 (11) pp. 714–716 (Abstract).
Rond et al 109CA:236901q 1988.
R. R. Allingham et al., "Topical Aminocaproic Acid Significantly Reduces the Incidence of Secondary Hemorrhage in Traumatic Hyphema in the Rabbit Model," *Laboratory Sciences*, 106, 1436–1438 (Oct. 1988).
H. E. Kaufman et al., eds., *The Cornea*, Churchill Livingstone, "Corneal Trauma," pp. 619–621 (1988).
H. M. Leibowitz, ed., *Corneal Disorders, Clinical Diagnosis and Management*, W. B. Saunders Company, pp. 222–227 (1984).
W. Tasman et al., ed., *Duane's Clinical Ophthalmology*, J. B. Lippincott Company, pp. 1–22, Revised Edition (1993).
Robert C. Arffa; "Epithelial Diseases, Chapter 15;" *Grayson's Diseases of the Cornea*; Kimberly Kist, ed.; 324–332 (1991).
Ramon R. Berrios et al., "Traumatic Hyphema," *International Ophthalmology Clinics, Trauma*, 35, 93–103 (1995).
Alvina M. Janda, "Ocular Trauma—Triage and Treatment," *Postgraduate Medicine*, 90, 51–52, 55–57, 59–60 (Nov. 15, 1991).
Bradford Shingleton, "Eye Injuries," *The New England Journal of Medicine*, 325, 408–413 (Aug. 8, 1991).
M. Verstraete, "Clinical Application of Inhibitors of Fibrinolysis," *Drugs—Focus on Flecainide and Terfenadine—Multiple Sclerosis Diuretics: A Review*, 29 236–261 (Jan. 1985).

Primary Examiner—Russell Travers
Attorney, Agent, or Firm—Schwegman, Lundberg, Woessner & Kluth, P.A.

[57] ABSTRACT

Persistent epithelial defects are effectively treated by topically applying a gelatinous composition containing either aminocaproic acid or tranexamic acid to the eye. In vivo results demonstrate improved healing of the epithelium and basement membrane complex. The gelatinous composition is prepared by a process that ensures sterility and proper pH conditions throughout the gel.

2 Claims, No Drawings

TOPICAL COMPOSITIONS FOR RE-EPITHELIALIZATION OF PERSISTENT EPITHELIAL DEFECTS

This is a continuation of application Ser. No. 08/055,717, filed Apr. 30, 1993, now abandoned.

BACKGROUND OF THE INVENTION

1. Field of the Invention

The present invention generally relates to a topical composition applied to the eye for the treatment of persistent epithelial defects (PEDs).

2. Description of the Prior Art $\epsilon$-Aminocaproic acid (ACA) and tranexamic acid (TA) are antifibrinolytic agents. Both drugs have been used in the treatment of traumatic hyphaema in the eye. The impetus for using these drugs to treat this disorder is the presumption that hemorrhages occur as a result of clot breakdown by fibrinolysis. The drugs have been administered orally to patients and experiments have been conducted with topically applied compositions containing the drugs.

SUMMARY OF THE INVENTION

It is an object of this invention to provide a topical composition useful in the treatment of PEDs.

According to the invention, it has been discovered that topically applied ACA improves healing of the epithelium and basement membrane complex. Similar results can be achieved with topical formulations which include TA.

DETAILED DESCRIPTION OF THE PREFERRED EMBODIMENTS OF THE INVENTION

After corneal abrasion, PEDs may occur due to the failure of regenerating epithelium to adhere to the underlying stroma. ACA inhibits activation of plasmin which metabolizes fibronectin, a glycoprotein that anchors ocular epithelium to the stroma. TA has similar effects.

PEDs were induced in experimental animals to demonstrate that topical formulations containing ACA improves the healing of the epithelium and basement membrane complex. To induce PEDs, filter paper disks saturated with 4N NaOH were placed for 2 min. on corneas of anesthetized rabbits. Seven days later, the majority of the corneas had areas denuded of epithelium.

Treatment began seven days after PED induction. Either 30% ACA or the vehicle (4% carboxypolymethylene powder) alone was administered topically three times daily. Rabbits were treated 5, 11, 16, or 19 days. As a control, another group received no ACA or vehicle. Assessment with fluorescein staining indicated that PEDs in rabbits treated with ACA for 19 days were 50% smaller than those from rabbits treated with vehicle alone. After 15 days, 100% of the control (untreated) rabbits had PEDs. Rabbits which received ACA had more pronounced healing during the first weak of treatment with even greater healing observed after 11 days of treatment.

Frozen sections, stained immunofluorescently for fibronectin, appeared to qualitatively contain more adherent fibronectin. Transmission and scanning electron microscopy showed more disrupted, thinner and vacuolated epithelium in untreated controls compared to ACA treated eyes. Light microscopy showed more continuous adherent epithelium after ACA treatment.

The study demonstrates that topical treatment of PEDs with ACA promotes re-epithelialization. Based on the similar modes of action, the same results should be achieved with topically applied TA.

Topically applied ophthalmic gel formulations within the practice of this invention include either 10–60 wt % ACA or 1–10 wt % TA. A suitable ophthalmic gel formulation containing 30% ACA within the scope of this invention can have the following ingredients: 30 grams ACA, 100 milligrams ethylenediamine tetraacetic acid (EDTA), 2 grams of carboxypolymethylene powder (available from BF Goodrich Co.), and 100 ml of sterile water. A suitable ophthalmic gel formulation containing 5% TA within the scope of this invention can have the following ingredients: 5 grams TA, 100 milligrams EDTA, 2 grams of carboxypolymethylene powder, and 100 ml of sterile water. The concentration of carboxypolymethylene powder can vary, but the topical formulation generally performs best when this component is within the range of approximately 0.5% to 5% by weight. Other gelatin forming polymer compounds may also be employed within the practice of this invention and should generally be present at less than 10% by weight. Other bacteriocidal agents or preservatives besides EDTA can be used within the practice of this invention and these agents or preservatives are typically used at levels less than 1% by weight and optimally ranges between 0.05% and 0.25% by weight.

The ophthalmic gel formulation is prepared according to a procedure that ensures suitable pH conditions within the gel, optimum ACA solubility and gel consistency, and sterility in the resulting product. First, the carboxypolymethylene powder is added to 25 ml of sterile water in an autoclavable container. Second, the pH of the carboxypolymethylene/sterile water mixture is then adjusted to approximately 2.5 by titration with HCl. Other sterilized acid solutions may also be used for this purpose. Achieving a low pH in the preparation process at this point is needed since it will prevent the carboxypolymethylene from forming a thick gel and makes both subsequent combining with ACA or TA and sterilization of the gel possible. Third, the carboxypolymethylene mixture is autoclaved to achieve sterility. Suitable autoclaving conditions include 250° F. for 30 minutes; however, the time and temperature for autoclaving can be varied significantly. The objective of autoclaving is to sterilize the carboxypolymethylene gel vehicle. Other sterilizing techniques such as radiation exposure may be possible; however, filter sterilization is not possible with gel formulations. Fourth, the ACA or TA and EDTA powders are dissolved in the remaining 75 ml of sterile water. Fifth, filter sterilize the ACA or TA/EDTA solution into the sterile carboxypolymethylene gel. This can be done with a final filter of 0.22 microns and serial filtration may be necessary. ACA cannot be heat sterilized since it both decomposes and discolors at the temperatures required for heat sterilization. Filter sterilization should be done in aseptically in a laminar air flow hood. Sixth, adjust the pH of the gel product to 7.4 by aseptically adding a sterile NaOH solution or other basic solution. The NaOH solution must contain the prescribed wt % of ACA or TA to produce a final product at that level (e.g., 30% ACA in the NaOH is used to achieve a final ophthalmic gel formulation product with 30% ACA). As above, the NaOH solution with ACA or TA can be filter sterilized using a 0.22 micron filter. High performance liquid chromatography (HPLC) has been performed to confirm the wt % ACA or TA final concentration. Seventh, prepare unit doses of the gel for administration to patients. A suitable unit dose could be prepared by adding 0.2 ml of the gel to each of several 1 ml Glaspak syringes where the syringes will be capped with a sterile tip. The shelf life of the topical ACA or TA formulation is at least two years.

The gel formulation may be improved by incorporating ACA or TA into liposomes such as those which may be created from soya lecithin, phosphatidyl choline, and other compounds. ACA is very water soluble and could be incorporated into lecithin liposomes. The size and shape of the lecithin liposomes could be adjusted by the addition of water. A particular advantage which is likely to arise from the incorporation of ACA or TA in lecithin liposomes is that they may allow for a sustained release of ACA or TA (e.g., ACA or TA will be released topically over a longer period of time since the release of ACA or TA will be a function of the time of breakdown for the lecithin liposomes). Increased concentrations of ACA or TA might be used with the lecithin liposomes to prolong the usefulness of the gel.

The formulation technique described above provides a number of advantages. First, the pH of the gel is adjusted to a level which is consistent with conditions in plasma and in the aqueous humor (e.g., pH 7.4). By adding NaOH, the acidity of ACA or TA is overcome. By first adjusting the gel to an acidic and flowable form (e.g., adjusting carboxypolymethylene solution to pH 2.5) and subsequently adding the basic (NaOH) solution, the formulation process assured that the basic solution (NaOH) would be evenly distributed in the gel, thereby achieving a uniform pH throughout the gel. In addition, the formulation process assured that the ACA was evenly dissolved and distributed throughout the gel. Precautions were taken not to dilute the concentration of ACA or TA in the gel by the addition of base. Second, the solubility and consistency of the gel formulated according to the seven step process has an optimum consistency. The solubility and consistency of the gel changes with the addition of ACA or TA. The consistency of the gel is very important to an efficacious formulation since, with gels that are too thin, the product does not remain in contact with the corneal epithelium, and, with gels that are too thick, the product does not spread over the corneal epithelium. Third, a sterilized product is produced in a two part process where the gel is heat sterilized and the ACA or TA is filter sterilized. In this way, decomposition of ACA or TA by heat sterilization is avoided. Moreover, the gel is sterilized by heat since filter sterilization of a gel is not possible.

Other vehicles and gels do not provide comparable results to the carboxypolymethylene gels described above. For example, a gel of similar consistency which was prepared with ethylene maleic anhydride (EMA) and ACA was found to be toxic.

While the invention has been described in terms of its preferred embodiments, those skilled in the art will recognize that the invention can be practiced with modification within the spirit and scope of the appended claims.

We claim:

1. A method of using ε-aminocaproic acid in the treatment of a persistent epithelial defect on the external surface of the cornea, wherein re-epithelialization is significantly delayed over normal healing time, comprising the step of: applying to the external surface of a patient's cornea comprising a persistent epithelial defect, a gelatinous formulation which includes 10–60% by weight of aminocaproic acid less than 10% by weight of a gelatin forming polymer compound, less than 10% by weight of a preservative or a bacteriocidal agent, and water.

2. The method of claim 1 wherein said step of applying is performed multiple times over a period of time sufficient to heal said persistent epithelial defects.

\* \* \* \* \*